(12) United States Patent
Forster et al.

(10) Patent No.: US 7,486,775 B2
(45) Date of Patent: Feb. 3, 2009

(54) TISSUE IRRADIATION DEVICE WITH AT LEAST ONE ELECTRON SOURCE AND NUMEROUS RADIATION HEADS

(76) Inventors: Jan Forster, Lindberghstrasse 30, D-85051 Ingolstadt (DE); Reinhold Müller, Ringstrasse 12, D-91080 Marloffstein (DE); Nils Achterberg, Kapellenstrasse 6, D-91233 Neunkirchen am Sand (DE)

( * ) Notice: Subject to any disclaimer, the term of this patent is extended or adjusted under 35 U.S.C. 154(b) by 38 days.

(21) Appl. No.: 11/767,697

(22) Filed: Jun. 25, 2007

(65) Prior Publication Data

US 2008/0083880 A1    Apr. 10, 2008

(30) Foreign Application Priority Data

Jun. 26, 2006 (DE) ............... 10 2006 029 557
Apr. 23, 2007 (DE) ............... 10 2007 019 355

(51) Int. Cl.
- *H01J 35/30* (2006.01)
- *H01J 35/08* (2006.01)
- *G21K 5/04* (2006.01)
- *G21K 5/10* (2006.01)
- *H05G 1/02* (2006.01)
- *A61N 5/10* (2006.01)

(52) U.S. Cl. ............ 378/137; 378/64; 378/65; 378/119; 378/121; 378/124; 378/196; 378/197; 250/492.3

(58) Field of Classification Search .......... 378/9, 378/10, 12, 64, 65, 68, 69, 98.6, 119, 121, 378/124, 137, 196, 197; 250/398, 492.3
See application file for complete search history.

(56) References Cited

U.S. PATENT DOCUMENTS

| | | | | |
|---|---|---|---|---|
| 4,292,563 A * | 9/1981 | Gabbay et al. | ............... | 378/124 |
| 4,352,021 A * | 9/1982 | Boyd et al. | ................. | 378/12 |
| 4,631,743 A * | 12/1986 | Tomimasu et al. | ......... | 378/138 |
| 4,914,681 A * | 4/1990 | Klingenbeck et al. | ......... | 378/12 |
| 5,172,401 A * | 12/1992 | Asari et al. | ................. | 378/10 |
| 5,260,581 A * | 11/1993 | Lesyna et al. | ............ | 250/492.3 |
| 5,267,294 A * | 11/1993 | Kuroda et al. | ................ | 378/65 |
| 5,490,193 A * | 2/1996 | Kuroda et al. | ................ | 378/10 |
| 5,504,791 A * | 4/1996 | Hell et al. | ................ | 378/10 |
| 5,654,995 A * | 8/1997 | Flohr | ......................... | 378/10 |
| 6,738,451 B2 * | 5/2004 | Avnery | ...................... | 378/64 |
| 7,167,540 B2 * | 1/2007 | Muller et al. | ................ | 378/65 |
| 7,233,644 B1 * | 6/2007 | Bendahan et al. | ............ | 378/57 |

OTHER PUBLICATIONS

Nils Achterberg and Reinhold G. Müller, "Multibeam tomotherapy: A new treatment unit devised for multileaf collimation, intensity-modulated radiation therapy," Med. Phys. 34(10), 3926-3942 (2007).*

* cited by examiner

*Primary Examiner*—Allen C. Ho
(74) *Attorney, Agent, or Firm*—Dority & Manning, P.A.

(57) ABSTRACT

A device for irradiating tissue encompassing at least one electron source for generating an electron beam, numerous radiation heads that are firmly and annularly arranged in a supporting frame around an isocenter of the device and emit radiation towards the isocenter, and one beam guidance system to guide the electron beam in the housing towards the radiation heads. The beam guidance system has been built as a polygon, especially as a pentagon arranged like a ring around the isocenter, in which case media for deflecting the electron beam have been placed at every corner point of the polygon.

17 Claims, 2 Drawing Sheets

TISSUE IRRADIATION DEVICE WITH AT LEAST ONE ELECTRON SOURCE AND NUMEROUS RADIATION HEADS

FIELD OF THE INVENTION

The present invention refers to a tissue irradiation device with at least one electron source for generating an electron beam and numerous radiation heads firmly arranged in a supporting structure. In this design, the radiation heads are annularly arranged around an isocenter of the device in which the tissue to be irradiated can be placed. The radiation heads emit radiation towards the isocenter. In addition, the device is equipped with a beam guidance system for leading and guiding the electron beam in the supporting structure to the radiation heads.

BACKGROUND OF THE INVENTION

Tissue irradiation units are well known from current technological advances. To achieve their aim, the patient is placed on a table in an isocenter of the irradiation device so his/her tissue can be irradiated. The irradiation device is equipped with a radiation source that generates radiation, which will eventually be guided to one or even several radiation heads located within the device. Generally, a device rotates the radiation heads around the object to be irradiated in such a way that the beams always reach the target volume sequentially from various directions. The target volume receives a relatively large radiation dose in this way, while the healthy surrounding tissue is protected. These known devices have the disadvantage that the precise rotation of the radiation heads is difficult to carry out from the technical viewpoint owing to the size of the masses to be moved.

In order to simplify a tissue irradiation device, EP 1 311 322 B1 suggests the firm arrangement of numerous radiation heads within a housing. What that invention foresees is a common radiation source for all radiation heads, in which case a radiation splitter splits the radiation to the various radiation heads. After the splitting, the individual beams are in each case deflected several times by a beam guidance system until they are finally guided to the radiation heads, which are largely arranged in the shape of a ring around the tissue to be irradiated. In this design, the arrangement of the radiation heads leads to a relatively large housing size.

SUMMARY

The task of the present invention is to suggest a tissue irradiation device with firmly attached radiation heads that has a simple and compact design. Objects and advantages of the invention are set forth in part in the following description, or may be obvious from the description, or may be learned through practice of the invention.

A tissue irradiation device is equipped with an electron source for generating an electron beam. Numerous radiation heads firmly arranged in a supporting structure and annularly arranged around the device's isocenter. A beam guidance system guides the electron beam in the supporting structure to the radiation heads, which emit radiation towards the isocenter of the device. In certain embodiments of the invention, the beam guidance system has been designed as a polygon that forms a ring around the isocenter. In every corner point of the polygon, media for deflecting the electron beam have been arranged. Preferably, a common electron source is foreseen so that only one electron beam is generated, which is then sequentially guided to the individual radiation heads.

According to a preferred execution of the invention, the beam guidance system has been designed as a symmetrical polygon. Preferably, five firmly attached radiation heads are foreseen for the device, so that the beam guidance system is executed as a pentagon. If a common electron source for all radiation heads has been foreseen, then the electron beam can be fed into the beam guidance system through a corner point, for example, and then be sequentially guided to the individual radiation heads. Since the beam guidance system has been developed in one only plane, the device can have a particularly compact design. As a result of this, the supporting structure extends only very little in axial direction. Since several radiation heads can irradiate either simultaneously or sequentially, it is not necessary to rotate the radiation emitters around the target volume. Preferably, sequential operation of the radiation heads has been foreseen, since in this case no radiation splitters are needed. Thus, the collimators can be already adjusted in the other radiation heads by a radiation head during irradiation, thereby achieving short irradiation times. It is not necessary to interrupt the electron beam. In addition, the simple and slender construction of the supporting structure allows one to lower the device's manufacturing costs.

According to a further design of the invention, it is advantageous for the media that deflect the electron beam to consist of deflecting magnets. As a result of this, it is possible to guide the electron beam easily in the supporting structure.

It is also advantageous for the beam guidance system to be equipped with media for deflecting the electron beam towards the radiation heads, which are preferentially executed as kicker device for the deflecting magnets. The design of the beam guidance system can be simplified as a result of this. Therefore, a deflecting magnet is found in every corner point of the polygon. The magnet deflects the beam towards the next deflecting magnet or deflects the electron beam towards the isocenter of the device with the help of its kicker device.

The deflected electron beams can in this case be directly oriented towards the target volume or—according to another preferred execution of the invention—to a braking target, so that high-energy X-rays are generated. For this purpose, a braking target has been assigned to each radiation head.

Besides, it is advantageous for each radiation head to be assigned a primary collimator with which the beam's cross-section can be restricted, thus allowing the shaping of the beam.

Another advantage is to allocate in each case a preferentially controllable multi-lamellar collimator to the radiation heads. As a result of this, it is very easily possible to regulate the radiation intensity, thus allowing a radiotherapy that is modulated by intensity as well.

To measure photon fluence in the radiation heads, it is advantageous to have one irradiation chamber allocated to each head. This makes it possible to measure the radiation intensity precisely, thereby allowing the user to regulate intensity modulation in a known way. Preferably, the irradiation chambers have been allocated in each case to the beam hole of the primary collimators and directly connected to them.

It is also advantageous for the irradiation chambers to be subdivided into sectors, thus allowing an accurate analysis of the generated radiation field with respect to homogeneity and radiation distribution.

According to a preferred further development of the invention, the electron source introduces the electron beam tangentially into the polygonal beam guidance system. The tangential feeding of the electron beam into the beam guidance system allows one to additionally limit the size of the supporting structure or device in the axial direction. Thus, apart from the ring-shaped beam guidance, the tangential introduction also contributes to the compact construction of the device.

It is additionally advantageous for the electron source to have at least one deflection device allocated for the electron beam. Preferentially, the deflection device or devices would then deflect the electron beam by 270° before it enters the beam guidance system. Preferably, the deflection device should be executed in such a way that it leads to double focusing both in spatial direction and in the energy distribution of the electron beam.

It would also be advantageous for the electron source to be a linear accelerator. If the acceleration track of the linear accelerator is arranged in the plane of the polygon, then the device construction can be quite compact.

Furthermore, it is advantageous for the supporting structure to be largely ring-shaped. Preferably, the supporting structure should have two parts, with an internal and an external supporting frame. In this case, the radiation heads are firmly attached to the internal supporting frame.

According to a further development of the invention, it is advantageous for the internal supporting frame with the radiation heads firmly attached to it to be rotatably stored in the external supporting frame. As a result of this arrangement, additional beam directions are possible. Preferentially, the internal supporting frame is stored on rollers to allow easy rotation.

If the internal supporting frame is arranged in two parts with an internal and external ring, the arrangement of the beam-guiding and generating parts is possible in a particularly easy way. For example, the corresponding recesses in the rings can be executed to make room for the radiation heads or collimators.

If five radiation heads are foreseen and therefore the beam guidance system is designed as a pentagon, then the internal supporting frame can be preferably rotated by an angle of +/−36°. As a result of this, any desirable beam direction is possible without jeopardizing the adjustment of the radiation heads. Owing to the covering of any beam direction in the full circle, it is possible to optimize dose distribution in the patient, thus protecting healthy tissue even further. Besides, it is also possible to achieve different beam directions with little effort and without needing to readjust the radiation heads.

Thanks to the beam guidance system arrangement in a polygon according to the invention, radiation heads and collimators can be arranged in a relatively reduced space—especially in a pentagon—thereby allowing the diameter of the patient's opening to be executed in larger size than in other state-of-the-art devices. Preferably, the diameter of the patient's opening should be between 80 cm and 120 cm. As a result of this, a very large free space for the patient's table is gained. In addition, the patient can be positioned in such a way that the center of the treatment volume overlaps with the isocenter of the device.

The arrangement of the beam guidance system and the radiation heads with the collimators according to embodiments of the invention also makes it possible to keep the device's axial extension to a minimum. Preferably, the entire supporting structure should have an internal and external supporting frame extending about 80 cm in an axial direction.

The small depth of the ring-shaped supporting structure in connection with the large diameter of the patient's opening allows a relatively large mobility of the patient's table. Preferably, the patient table of the device should be adjusted horizontally and/or vertically with respect to the supporting structure.

Besides, it is advantageous if the patient's table has been arranged in the device so it can be swiveled. Preferably, the patient's table should be swiveled around a horizontal axis cutting through the isocenter. It is best if the patient's table can be swiveled up to +/−54° along a horizontal plane. This allows a non-coplanar radiation therapy, which can be especially used from intracranial stereo-tactic beam guidance all the way to radiosurgery. As a result of this, advantageous dose distributions can be carried out compared to the coplanar technique.

It is advantageous for the patient's table to be executed as a six-axis table, thus allowing any desired position of the target volume. The large patient's opening makes it possible to have various adjustments without the patient making contact with the shell of the support structure.

If the patient's table has been executed as a six-axis table, then a fully automated correction of the patient's position with respect to the isocenter of the device is also possible.

It is especially advantageous if the device for the fully automated positioning correction is equipped with an optical scanning system. The needed displacement vectors for positioning correction can be automatically calculated and carried out by the table by comparing the surface coordinates calculated through a comparison with the coordinates from a planning CT.

To facilitate an image-supported radiation therapy, an advantageous further development of the invention makes it make possible to link up the device with another unit such as a computer tomograph, preferably in a structural unit. However, a separate unit on rollers can also be likewise attached to the device as a "sliding gantry" for tissue irradiation.

Furthermore, it is advantageous for the supporting structure to have in each case radiation-absorbing masses opposite the radiation heads. As a result of this, inner radiation protection can be achieved, thereby making thinner bunker components possible. It is also advantageous for the internal supporting frame and/or external supporting frame to be built at least partly from a radiation-absorbing material.

According to a further design of the invention, the kinetic energy of the electrons that make up the electron beam can be adjusted. Likewise, the device can also encompass two electron sources, but in this case the kinetic energy of the generated electrons varies.

Additional advantages of the invention are described with the help of the execution examples listed below, which show:

DESCRIPTION

Figure 1:
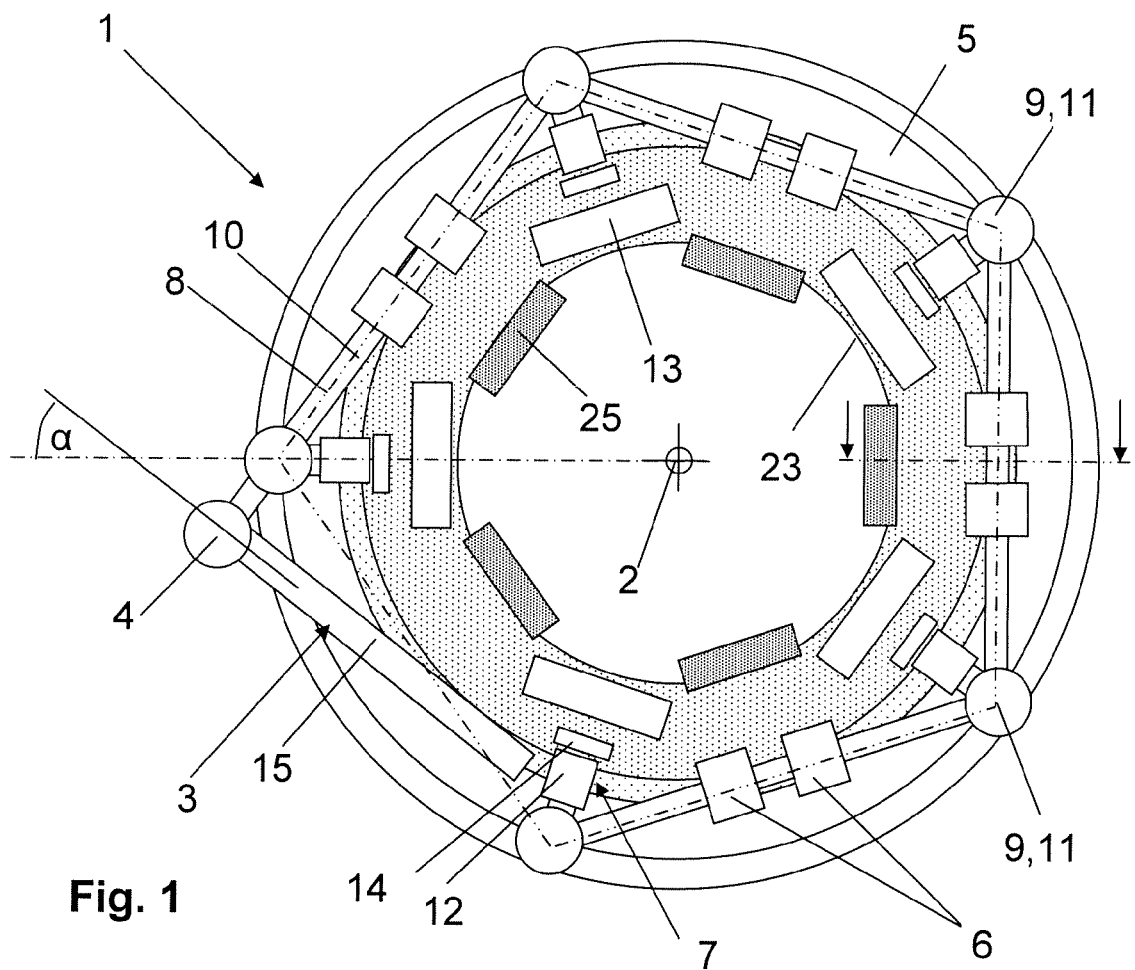
FIG. 1 a diagrammatic sectional view through a device used for tissue irradiation with a supporting structure, beam-guidance system and radiation heads, FIG. 2 a diagrammatic sectional view of a cross-section through the supporting structure of the device, FIG. 3 an exploded view of the internal supporting frame of the supporting structure, FIG. 4 an exploded view of the external ring of a two-part internal supporting frame.

Reference will now be made to embodiments of the invention, one or more examples of which are illustrated in the drawings. Each embodiment is presented by way of explanation of the invention, and not as a limitation of the invention. For example, features illustrated or described as part of one embodiment may be used with another embodiment to yield still a further embodiment. It is intended that the invention include these and other modifications and variations of the embodiments described herein.

FIG. 1 shows a device 1 for tissue irradiation that can be used especially for tumor radiation therapy. To achieve this, a patient can be placed in such a way on a patient-positioning table (not shown here) in the interior of the largely ring-shaped device 1, such that the target volume to be irradiated is located in the middle of the device 1, the isocenter 2. The device 1 is equipped with an electron source 3, executed here as a linear accelerator. The electron beam generated in a deflection device 4 in accordance with this view is deflected and finally fed tangentially into a supporting structure 5 executed largely in the shape of a ring that forms part of the device 1. The deflection by a total of 270° is advantageous, and in this case the deflecting magnet—if correspondingly executed—allows a so-called double focusing in spatial direction, which affects the electron beam's energy distribution.

Additionally, numerous radiation heads 7 have been firmly arranged largely in the shape of a ring around the isocenter 2 of the supporting structure 5 that forms part of the device 1. The radiation heads 7 emitting radiation towards the isocenter 2 of the device encompass in each case at least the primary collimators 12 and, if need be, a breaking target (not shown here). The invention foresees the electron beam 8 fed into the supporting structure 5 to be led and deflected by deflecting media in such a way that a polygonal beam guidance is created in the supporting structure 5, here having the shape of a pentagon. To achieve this, electron beam deflecting media executed here as deflecting magnets 9 have been arranged at every corner point of the polygon 10. It is better for the beam-guidance system to have the shape of a symmetrical polygon 10, but an asymmetrical design is also possible. Furthermore, geometrical optics elements 6 for beam guidance are arranged in each case between the deflection devices.

In order to guide the electron beam 8 to the individual radiation heads 7, more media for deflecting the electron beam to the radiation heads 7 are foreseen. In this example, the electron beam deflection media have been executed as deflecting magnets 9 that are also equipped with a kicker device 11 to deflect the electron beam 8 towards the radiation heads 7.

The beam guidance system according to the invention (which is shaped like a polygon 10, especially as a pentagon) allows the supporting structure 5 of the device 1 to be ready for use having a relatively small axial extension, which allows the device 1 to have a simple and compact design. To carry out several irradiation directions, it is not necessary to rotate the radiation heads 7 around the isocenter 2. At the same time, the ring-shaped beam guidance—that according to the invention has the shape of a polygon 10—makes it possible to supply several radiation heads 7 with only one electron source 3. As a result of this, the design of the device 1 can additionally be kept very compact.

In the illustration shown, the deflecting magnets 9 can be sequentially controlled, so that the radiation heads 7 can be sequentially controlled as well. However, a beam division in the corner points of the polygon 10 can also be foreseen, in which case a part of the beam would be deflected towards a radiation head 7, while the other beam would be deflected towards the next corner point of the polygon 10 by the deflecting magnet 9.

The electron beam 8 deflected towards the radiation heads 7 can be guided directly to the target volume in the isocenter 2 of the device 1 as useful radiation after the corresponding beam shaping, but it is also possible to allocate in each case a braking target (not shown here) to the radiation heads 7 for the generation of X-rays.

One primary collimator 12 has been allocated in each case to the radiation heads 7 in order to shape the beam and restrict it to the target volume. So an intensity-modulated radiation therapy (IMRT) can be carried out, controllable multi-lamellar collimators 13 (FIG. 3) have in each case also been allocated to the radiation heads 7 according to the example shown. These collimators allow irregular field shapes to be generated, so that the distributed dose can be optimally adapted to the target volume.

To regulate the quantity of radiation, irradiation chambers 14 have also been arranged in the beam holes of the primary collimators 12. These chambers are preferentially connected directly to the primary collimators 12. The irradiation chambers 14 are subdivided into several sectors so that the irradiated dose as well as the homogeneity and uniform distribution of the radiation field can be calculated. Deviations from the values set earlier can therefore be determined and corrected.

Thanks to the tangential feeding of the electron beam 8 into the supporting structure 5, the design of the device 1 can kept largely compact. This compact construction of the device 1 can additionally be supported by arranging the acceleration track 15 of the linear accelerator 3 in such a way on the plane of the polygon that a direct tangential feeding is possible. In the example shown, the first radiation head has been arranged so that the direction of its beam is guided exactly horizontally. The acceleration track 15 has therefore been arranged at an angle $\alpha$ of 36° (in this pentagonal beam guidance system) with respect to the horizontal. Thus, only the deflection of the electron beam 8 towards the radiation head 7 takes place in the first deflecting magnet 9.

Figure 2:
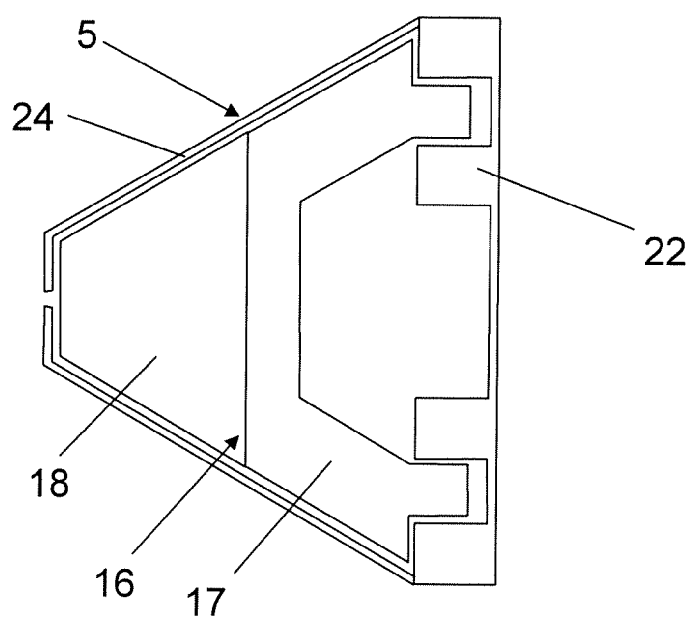

The supporting structure 5, in which the radiation heads 7 are firmly arranged, has a largely annular shape. The supporting structure 5 is preferably executed in two parts, with an internal supporting frame 16 and an external supporting frame 22 (FIG. 2). Preferably, the internal supporting frame 16 consists of an external ring 17 and an internal ring 18.

Figure 3:
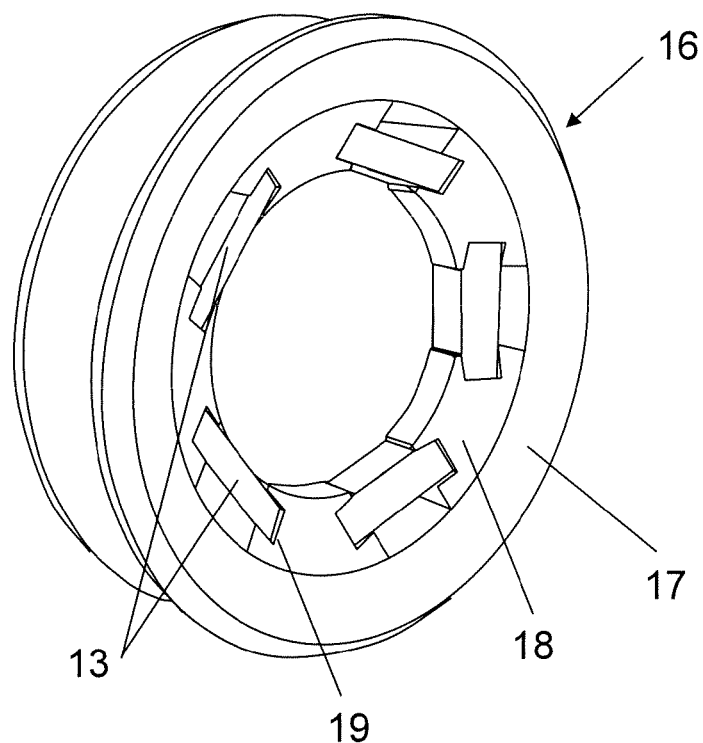
Figure 4:
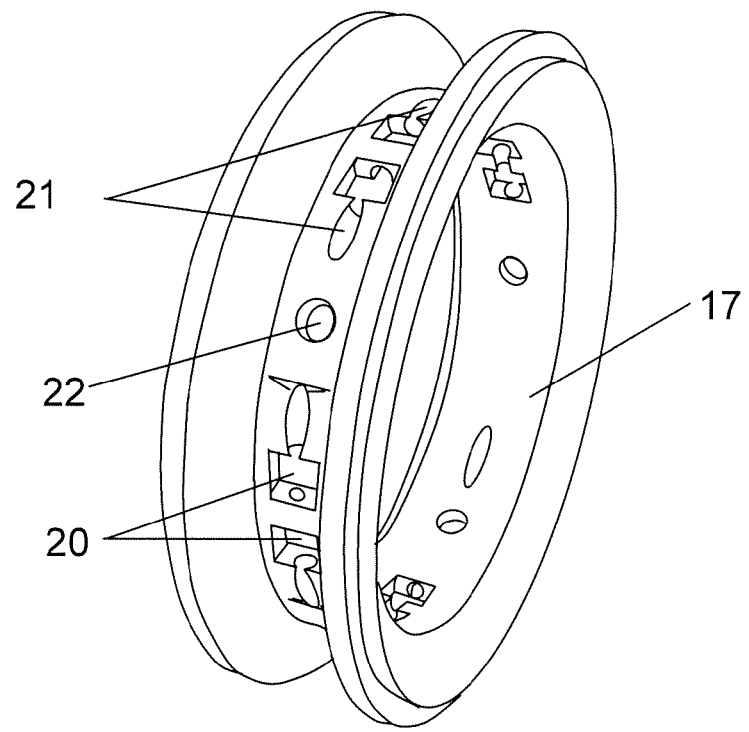

FIG. 3 shows an exploded view of the internal supporting frame 16 of the supporting structure. In the external and internal rings 17, 18 various recesses 19 have in each case been arranged, in which the components for the beam guidance system and the radiation heads can be built in. As can be seen in the illustration of FIG. 4, recesses 20 for the geometrical optics elements 6, recesses for the beam guidance system in the form of a pentagon 21 and recesses 22 for the primary collimators 12 have been built in the external ring 17.

On the other hand, mostly recesses 19 for the multi-lamellar collimators 13 have been foreseen for the internal ring 18.

In order to cover a full circle with regard to the beam direction that can be carried out with the radiation heads 7, the internal supporting frame 16 consisting of the internal and external rings 17 and 18 can be rotatably arranged in a largely ring-shaped external supporting frame 22, as can be seen in FIG. 2. Preferentially, the internal supporting frame 16 is stored in the external supporting frame 22 on rollers (not shown here), and as far as this pentagonal beam guidance system is concerned, it can be rotated by an angle of +/−36°.

The tangential feeding of the electron beam 8 according to the invention and the annular beam guidance system in the shape of a polygon 10, allow the annular structure of the supporting structure 5 to be executed in a highly compact way, which creates plenty of available space for the patient's table. Thus, the diameter of the patient's opening can be 23 to 120 cm, which exceeds all comparable state-of-the-art units as a result of this (in the others, the diameter for the patient's opening is just 80 cm). In the axial direction, the supporting structure 5 only extends a little as well, to about 80 cm, as seen in FIG. 2. Additionally, the arrangement of the beam guidance system and radiation heads 7 according to the invention allows the supporting structure 5 to taper towards the patient opening 23, thereby allowing the patient's table to be moved a great deal. Thus, the patient's table can be moved horizontally as well as vertically without the patient making contact with the shell 24 of the supporting structure 5. The tapered shell 24 allows the patient's table to be swiveled up to +/−54° on a horizontal plane, thus allowing a non-coplanar radiation therapy as well. The dimensions of the device 1 according to the invention for tissue irradiation also allow the patient's table to be built as a six-axis table, so that banking and pivoting angles can also be carried out for the table.

The execution of the patient's table as a six-axis table also allows the fully automated correction of the patient's position. To achieve this, the device 1 has been equipped, for example, with an optical scanning system according to DE 198 05 917. In this case, the patient's surface coordinates resulting from his/her current position are compared with the initial values of the planning CT, from which finally the six displacement vectors for the patient's table are obtained. Thanks to this system, the patient's position can be quickly corrected without endangering the patient in any way. The automatic positioning correction allows at least something approaching an image-supported irradiation. Expenses for additional CT measurements can be reduced as a result of this.

Since the supporting structure 5 of the device 1 according to the invention for tissue irradiation is very compact in its axial extension, the device 1 can be easily linked up to another unit such as a computer tomograph. As a result of this, image-supported irradiation or image guided radiation therapy can be carried out without any restrictions. In this case, the computer tomograph can be attached to the device 1 as a "sliding gantry" on rollers or also be integrated to it to form one single unit.

In order to reduce the radiation emitted from the device 1, it is advisable to equip the device 1 with beam stoppers for internal radiation protection. To achieve this, the internal supporting frame 16 or the internal ring 18 and external ring 17 can be made from a radiation-absorbing material such as steel, Wood's metal, lead or other heavy components. Thus, the supporting frame 16 can be made of ductile nodular cast iron, for example, since it can resists mechanical load, is weldable and can be mechanically processed without difficulty. It is also conceivable to arrange radiation-absorbing masses 25 in the supporting structure 5, in each case opposite the radiation heads 7 (see FIG. 1). In addition, it is possible to manufacture at least some parts of the external supporting frame 22 from a radiation-absorbing material.

According to a further variant not shown here, steel blocks acting as radiation-absorbing masses 25, for example, can be mounted onto the external ring 17, at the same time foreseeing a lateral insert for the multi-lamellar collimators 13.

The invention is not restricted to the execution examples shown. Modifications and combinations within the scope of the patent claims also fall under the invention.

The invention claimed is:

1. A device for irradiating tissue, comprising:
an electron source;
a supporting structure having a plurality of radiation heads arranged thereon around an isocenter so as to emit radiation towards said isocenter;
a guidance system configured in said supporting structure as a ring-shaped polygon with a plurality of corner points around said isocenter to direct an electron beam from said electron source to said radiation heads; and
media disposed at each of said corner points to deflect said electron beam.

2. The device as in claim 1, wherein said media comprises a deflecting magnet at each of said corner points.

3. The device as in claim 2, wherein said deflecting magnet comprises a kicker device that deflects the electron beam to one of said radiation heads.

4. The device as in claim 1, wherein each of said radiation heads further comprise a braking target for generating X-rays.

5. The device as in claim 1, further comprising a primary collimator and an irradiation chamber at each of said radiation heads, said irradiation chamber directly connected to a respective said collimator.

6. The device as in claim 5, wherein said irradiation chamber is subdivided into sectors.

7. The device as in claim 1, wherein said electron source is common to all of said radiation heads and is disposed so that the electron beam is directed tangentially by at least one deflection device into said guidance system.

8. The device as in claim 7, wherein said deflections is disposed so as to deflect the electron beam by 270° into said guidance system.

9. The device as in claim 7, wherein said deflection device comprises a double-focusing deflection device.

10. The device as in claim 1, wherein said electron source comprises a linear accelerator arranged in the plane of said guidance system.

11. The device as in claim 1, wherein said supporting structure comprises an external supporting frame and an internal supporting frame rotatably mounted within said external supporting frame, said radiation heads fixed to said internal supporting frame.

12. The device as in claim 11, wherein said internal supporting frame comprises internal and external rings.

13. The device as in claim 11, wherein said supporting structure measures about 80 cm in an axial direction, said device comprising a patient opening between about 80 cm and 120 cm.

14. The device as in claim 11, wherein at least portions of said supporting structure are made of a radiation absorbing material.

15. The device as in claim 1, further comprising a patient table that is horizontally, vertically, or rotationally adjustable relative to said supporting structure.

16. The device as in claim 15, further comprising an optical scanning system configured with said patient table for automated correction of said table with respect to a patient's position relative to said isocenter.

17. The device as in claim 1, further comprising radiation-absorbing masses arranged in said supporting structure generally opposite from said radiation heads.

* * * * *